United States Patent
Kawakatsu et al.

(10) Patent No.: US 7,540,292 B2
(45) Date of Patent: Jun. 2, 2009

(54) DETERGENT FOR WASHING A SELECTIVELY PERMEABLE MEMBRANE AND METHOD OF WASHING

(75) Inventors: Takahiro Kawakatsu, Atsugi (JP); Nobuhiro Orita, Yokohama (JP); Naoto Hitotsuyanagi, Kanagawa (JP)

(73) Assignee: Kurita Water Industries Ltd., Tokyo (JP)

( * ) Notice: Subject to any disclaimer, the term of this patent is extended or adjusted under 35 U.S.C. 154(b) by 0 days.

(21) Appl. No.: 10/545,884

(22) PCT Filed: Feb. 23, 2004

(86) PCT No.: PCT/JP2004/002078

§ 371 (c)(1),
(2), (4) Date: Aug. 24, 2006

(87) PCT Pub. No.: WO2004/076040

PCT Pub. Date: Sep. 10, 2004

(65) Prior Publication Data

US 2007/0015680 A1 Jan. 18, 2007

(30) Foreign Application Priority Data

Feb. 25, 2003 (JP) .............................. 2003-048170

(51) Int. Cl.
*B08B 9/027* (2006.01)
*B08B 3/04* (2006.01)
*C11D 3/20* (2006.01)
*C11D 3/43* (2006.01)

(52) U.S. Cl. .................. 134/22.19; 134/38; 134/39; 134/40; 134/42; 510/162; 510/200; 510/505

(58) Field of Classification Search .............. 510/162, 510/200, 505; 134/22.19, 38, 39, 40, 42
See application file for complete search history.

(56) References Cited

U.S. PATENT DOCUMENTS 4,153,545 A * 5/1979 Zwack et al. ............. 134/22.18
5,076,896 A * 12/1991 Carduck et al. ............... 203/41
6,235,692 B1 * 5/2001 Scoville et al. .............. 510/160

FOREIGN PATENT DOCUMENTS

JP          52-125475         10/1977

(Continued)

OTHER PUBLICATIONS

Pohle et al, "Analysis of Mixtures of Glycerol, Propylene Glycol, and Trimethylene Glycol", The Journal of the American Oil Chemists' Society, p. 155, May 1947.*

*Primary Examiner*—Brian P Mruk
(74) *Attorney, Agent, or Firm*—Flynn, Thiel, Boutell & Tanis, P.C.

(57) ABSTRACT

A detergent and a method for washing applicable to selectively permeable membranes for proposed, which can attain washing of selectively permeable membranes deteriorated in its membrane performance, such as the flux, in an efficient manner within a brief time at a higher detergent effect without causing deterioration of the selectively permeable membranes and without damaging safety to human and to environment with superior handling aspect.

The detergent contains a polyol having a molecular weight not higher than 400 and, if necessary, an organic solvent.

6 Claims, 5 Drawing Sheets

FOREIGN PATENT DOCUMENTS

| | | |
|---|---|---|
| JP | 58-045712 | 3/1983 |
| JP | 58-119304 | 7/1983 |
| JP | 04-193333 | 7/1992 |
| JP | 08-281081 | 10/1996 |
| JP | 09-313901 | 12/1997 |
| JP | 11-212274 | 8/1999 |
| JP | 2000-325758 | 11/2000 |
| JP | 2001-161811 | * 6/2001 |
| JP | 2003-001073 | 1/2003 |

* cited by examiner

DETERGENT FOR WASHING A SELECTIVELY PERMEABLE MEMBRANE AND METHOD OF WASHING

FIELD OF THE INVENTION

The present invention relates to a detergent for washing a selectively permeable membrane, such as a reverse osmosis membrane, nano-filtration membrane and the like, and to a washing method using such a detergent. More particularly, it relates to a detergent for washing a selectively permeable membrane, of which its performance, such as flux (permeation flow flux) and so on, has deteriorated by being contaminated through treatment of, for example, concentration of a solution, desalting, water treatment, such as production of pure water, and other treatments, for recovery of performance, a well as to a method of washing by using such a detergent.

BACKGROUND OF THE INVENTION

When a selectively permeable membrane, such as a reverse osmosis membrane, ultrafiltration membrane or the like, is used for, for example, concentration of a solution, desalting, production of pure water and other water treatment, the selectively permeable membrane will be contaminated by various pollutant substances, whereby it suffers from a decrease in the flux to cause a reduction in the selective permeability. Therefore, it has been practiced to wash such a selectively permeable membrane deteriorated in its performance using a detergent in order to recover the performance.

Hitherto, it has often been practiced to use an acid, alkali, organic solvent or surfactant as a detergent for washing a selectively permeable membrane deteriorated in its performance, such as flux. For example, Japanese Patent Kokai Sho-54-99783 A discloses a washing technique using an alkali as the detergent, by which it is difficult, due to severe contamination, to recover the flux within a brief time and the degree of flux recovery will never reach to 100%.

In Japanese Patent Kokais Sho-52-125475 A and Sho-58-119304 A and in others, a technique is disclosed in which an organic solvent is used at higher concentrations. However, this technique involves a danger of causing deterioration of the membrane or the membrane module, though a high washing effect may be attained for the case where the pollutant is an organic substance, so that the present situation is in that this technique is not applicable to practical apparatuses. For example, an organic solvent, such as methanol, ethanol or acetone, has a high washing ability for a reverse osmosis membrane or for a nano-filtration membrane, however, it causes, at higher concentrations, deterioration of the membrane or the membrane module. There is a problem that a high detergent effect is not attainable at a concentration not causing deterioration of the membrane or the membrane module.

In Japanese Patent Kokai Sho-55-51406 A, a washing technique using alkyl ethers of ethylene glycol is disclosed. However, alkyl ethers of ethylene glycol have both hydrophilic and hydrophobic groups and exhibit molecular structures close to monohydric alcohol. They are highly detrimental and emit a strong irritating smell and, hence, they are designated in the Law of PRTR (Environmental Pollution Release and Transfer Registration) and prescribed for their work environment assessment level to be not higher than 5 ppm, whereby there is a problem that a high application concentration is not allowed.

The object of the present invention is to propose a detergent for washing a selectively permeable membrane and a method for washing, with which it is able to realize a high detergent effect for a selectively permeable membrane and to cause no deterioration of the selectively permeable membrane and which are safe, not only for humans but also for the environment with superior handling easiness, and can wash a selectively permeable membrane having a deteriorated performance, such as the flux and so on, efficiently within a brief time to enable restoration of the performance.

DISCLOSURE OF THE INVENTION

The present invention consists in the following detergent for washing of a selectively permeable membrane and method for washing:

(1) A detergent for washing a selectively permeable membrane, comprising a polyol having a molecular weight not greater than 400.

(2) The detergent as defined in the above (1), wherein it further comprises an organic solvent.

(3) The detergent as defined in the above (1) or (2), wherein the polyol is selected from the group consisting of ethylene glycol, diethylene glycol, propylene glycol, glycerin, polyglycols and sugar alcohols.

(4) The detergent as defined in the above (2) or (3), wherein the organic solvent comprises a compound selected from the group consisting of monohydric alcohols, ethers, ketones and amides.

(5) The detergent as defined in any one of the above (1) to (4), wherein the selectively permeable membrane to be washed is one which is contaminated with a polymeric polyalkylene glycol and/or non-ionic surfactant of a molecular weight greater than 400 adhering thereto.

(6) A method for washing a selectively permeable membrane exhibiting a deteriorated flux, comprising washing the membrane with a washing liquid comprising a polyol having a molecular weight not greater than 400.

(7) The method as defined in the above (6), wherein the washing liquid contains further an organic solvent.

(8) The method as defined in the above (6) or (7), wherein the membrane is subjected, before and/or after the washing with the washing liquid, to a pretreatment washing and/or an after-treatment washing by another washing method.

(9) The method as defined in any one of the above (6) to (8), wherein the washing is performed by contacting the washing liquid with the selectively permeable membrane.

The selectively permeable membrane to be washed according to the present invention is one in which any performance, such as flux, selective permeability or the like has been decreased. Here, the selectively permeable membrane refers to a semipermeable membrane, such as a reverse osmosis membrane, nano-filtration membrane or the like, which permits the permeation of specific substances, components and others, selectively, wherein there is no limitation in their application and they are applied for general uses. As to the material of the selectively permeable membrane, there is no special limitation and, for example, permeable membranes based on polyamides, polysulfones, polyimides and celluloses may be enumerated. The object to be washed may be not only a selectively permeable membrane itself but also a membrane module. There is no special limitation for the membrane module to be washed and there may be recited, for example, a tubular membrane module, a flat membrane module, a spiral membrane module and a hollow fiber membrane module.

It is no matter what the cause may be for the decrease in the performance of the selectively permeable membrane, but the decrease in the performance is caused, in general, due to contamination through the use of the reverse osmosis membrane for, for example, concentration of a solution, desalting, water treatment, such as the production of pure water and so on, process treatment and other treatments. Also, there is no special limitation as to the contaminant substances and every contaminant of organic or inorganic nature may come into consideration, while the detergent effect is superior, especially for objects contaminated by adhering polymeric contaminants of polyalkylene glycol or a nonionic surfactant of a molecular weight of at least 400.

Polyalkylene glycol, such as polyethylene glycol, polypropylene glycol and so on, especially polyethylene glycol, or nonionic surfactants composed of such polyalkylene glycols, will adhere onto the surfaces or the fine pores of the selectively permeable membrane due to their high affinity to selectively permeable membranes and cause deterioration of the membrane performance. Among them, those having molecular weights not higher than 400 will easily be washed out by water wash or the like due to their high hydrophilicity, whereas selectively permeable membrane contaminated, by adhering thereto, with polymeric contaminants of polyalkylene glycols or nonionic surfactants having molecular weights greater than 400 will not attain removal of the adherent contaminants by permeation of water and may cause a deterioration of performance due to the difficulty of being washed out and removal thereof with water.

The inventors had performed repeated researches as to the washing of selectively permeable membranes contaminated with such contaminants and obtained the knowledge that a material to be used as the detergent should have OH group and that a material having, in particular, plural OH groups is effective in removing such member contaminants. The present invention has been completed based on such knowledge.

The detergent for washing a selectively permeable membrane according to the present invention comprises a polyol of a molecular weight not higher than 400 and preferably comprises further an organic solvent in addition to the polyol. The detergent for washing the selectively permeable membrane according to the present invention may further comprise other component(s). The detergent for washing of the selectively permeable membrane according to the present invention may often be used in practice as an aqueous solution, though it may not contain water in the form of a product of manufacture.

The polyol is a compound having a plurality of OH groups, for which there may be exemplified alkylene glycols, such as ethylene glycol, propylene glycol, trimethylene glycol and the like; glycerin; polyglycols, such as diethylene glycol and other polyalkylene glycols; and sugar alcohols, such as erythritol, mannitol and the like. For the above polyols, preference is given to hydrophilic ones, wherein those having a number of carbon atoms of 2 to 6 and OH/C ratio in the range of 0.5 to 1 are preferred. These polyols may be used alone but preferably are used in a mixture of two or more of them, as the detergent effect is thereby increased. In the case where the contaminant substances include a nonionic surfactant, it is preferable to use a polyalkylene glycol, such as diethylene glycol, concurrently with other polyol(s) in order to increase the solubility of the nonionic surfactant to improve the detergent effect.

For the organic solvent to be used together with the polyol, those which have conventionally been used, such as monohydric alcohols, ethers, ketones and amides, may be employed. For the organic solvents, polar ones are preferred, wherein those of carbon numbers of 1-3 are preferable. For the monohydric alcohols, there may be recited, for example, methanol and ethanol. For the ethers, there may be recited, for example, ethers of the above-mentioned monoalcohols or polyols. For the ketones, there may be recited, for example, acetone, acetylacetone and so on. For the amides, there may be recited, for example, formamide and so on. Also, these organic solvents may be used alone but preferably are used in a mixture of two or more of them.

The polyol and the mixture of the polyol with an organic solvent to be used as the detergent for washing selectively permeable membrane may be each used in a state without a water content but may be used in a form of an aqueous solution. The concentration of the aqueous solution may not specifically be restricted, while it may, in general, be in the range of from 15 to 90% by weight, preferably from 35 to 60% by weight. In the case of using a polyol and an organic solvent, usually, the polyol may be in a proportion of 10-70% by weight, preferably 30-60% by weight, and the organic solvent may be in a proportion of 5-30% by weight.

Using a polyol solely as the detergent, the contaminants can be washed out and removed while, in some cases, it is rather preferable to use a polyol and an organic solvent concurrently in order to reduce the operation cost or to improve the washing effect. An organic solvent has hitherto been used and thereby a superior washing effect has been attained, however, it brings about a problem that it may cause a deterioration of the selectively permeable membrane due to the inevitable use thereof at higher concentrations and is not safe to humans and to the environment together with inferior aspects in handling. In contrast thereto, use of an organic solvent in a mixture with a polyol permits the reduction of the application concentration of the organic solvent to thereby avoid such a problem and, in addition, can attain a synergistically superior washing effect.

The method for washing of a selectively permeable membrane according to the present invention consists in washing a selectively permeable membrane having a deteriorated performance, such as flux, with a washing liquid comprising the above-mentioned polyol or with a washing liquid comprising the polyol and the organic solvent. One specific practice of the washing method comprises bringing the selectively permeable membrane into contact with the washing liquid, in which soaking in the washing liquid or washing in laminar flow or in a turbulent flow may be preferable, though washing by permeating the washing liquid through the selectively permeable membrane may also be possible.

There is no special limitation for the pressure applied during the washing. In the case of soaking, application of any pressure is unnecessary. In the case of washing in laminar or turbulent flow or by permeation, a pressure not higher than that during the permeation of the liquor-to-be-treated in service run may be applied. The duration of the washing operation, namely, the time held under contact with the washing liquid, may vary according to each specific condition of the degree of the deterioration, the concentration of the washing liquid or so on, while it may be, in general, in the range from 1 to 8 hours.

By carrying out the washing by the washing liquid mentioned above, the contaminants adhering onto the selectively permeable membrane will dissolve in the washing liquid and are eluted out, whereby the deteriorated performance of the selectively permeable membrane, such as the flux, the selective permeability and so on, can be restored. The detergent according to the present invention brings about a higher detergent effect for a selectively permeable membrane without causing deterioration of the selectively permeable membrane and is safe to humans and the environment, with a superior handling aspect and can wash a selectively permeable membrane having a deteriorated performance, such as the flux, efficiently within a brief time to restore the performance.

Here, the selectively permeable membrane may be deprived of not only the contaminants attached adheringly thereto during the service use but also the pollutant substances having adhered originally thereto before the service use, whereby the degree of recovery of the membrane performance may occasionally exceed 100%.

The polyol having a molecular weight not higher than 400 contained in the detergent according to the present invention exhibits a strong affinity not only to water but also to polymeric alkylene glycols or to nonionic surfactants, so that it provides a high detergent effect even for contaminants constituted of polyalkylene glycol or nonionic surfactants of molecular weights higher than 400 adhering onto the selectively permeable membrane, whereby the contaminants are washed away efficiently within a brief time by dissolving in the washing liquid to attain recovery of the membrane performance without causing any deterioration of the selectively permeable membrane.

According to the present invention, it is preferable that the membrane is subjected, before and/or after the washing with the washing liquid, to a pretreatment washing and/or an aftertreatment washing by another washing method including the use of other washing liquids, for example, water, an alkali, such as sodium hydroxide, or an acid, such as sulfuric acid; and physical washing method, such as ultrasonic cleaning. The pretreatment washing provides a preliminary cleansing as a pretreatment by using another washing liquid or washing technique to effect preliminary release or to render ease of release of the adherent contaminants. For instance, when the contaminants are adhering firmly, they can be brought to a state where they are easy to be detached, by effecting, for example, cleansing with other washing liquids, such as an alkali solution, or ultrasonic wave irradiation, in order to make easy the washing by the detergent.

The aftertreatment washing provides a supplementary washing as an aftertreatment by using another washing liquid or washing technique to remove the remaining detergent and the detached contaminant remainders. A water wash may be enough for a case where the rest of the low molecular weight polyol used as the detergent remains. However, as the molecular weight of the polyol comes closer to 400, it tends to be detained more facilitatedly. The remaining polyol can easily be removed by washing with an alkaline washing liquid. While the concentration of alkali in the alkaline washing liquid may voluntarily be chosen, it may be an aqueous solution having a pH preferably in the range of from 9 to 12. Any voluntary washing technique may be employed using such an alkaline solution and a technique similar to that using the washing liquid mentioned above can be employed.

By further washing with other washing liquids after the proper washing with the washing liquid according to the present invention, the contaminants remaining without being removed by the washing liquid are washed out and removed, whereby the performance of the selectively permeable membrane is recovered sufficiently and any elution of contaminants in the subsequent treatment course can be prevented. The washing method according to the present invention can be realized in combination with other washing techniques using other washing liquids.

Since the detergent for the washing of selectively permeable membranes according to the present invention comprises a polyol having a molecular weight not higher than 400, a high detergent effect for a selectively permeable membrane is attained without deteriorating the selectively permeable membrane and without damaging the safety to humans and to the environment with a superior handling aspect and the selectively permeable membrane deteriorated in its membrane performance can be washed efficiently within a brief time to recover the membrane performance.

The method for washing a selectively permeable membrane according to the present invention employs the above-mentioned detergent, so that it realizes efficient washing of a selectively permeable membrane deteriorated in its membrane performance at a high detergent effect safely within a brief time without deteriorating the selectively permeable membrane with a superior handling aspect to enable the recovery of the membrane performance.

THE BEST MODE FOR EMBODYING THE INVENTION

Below, the present invention will be described by way of mode of embodiment with reference to the appended drawings.

Figure 1:
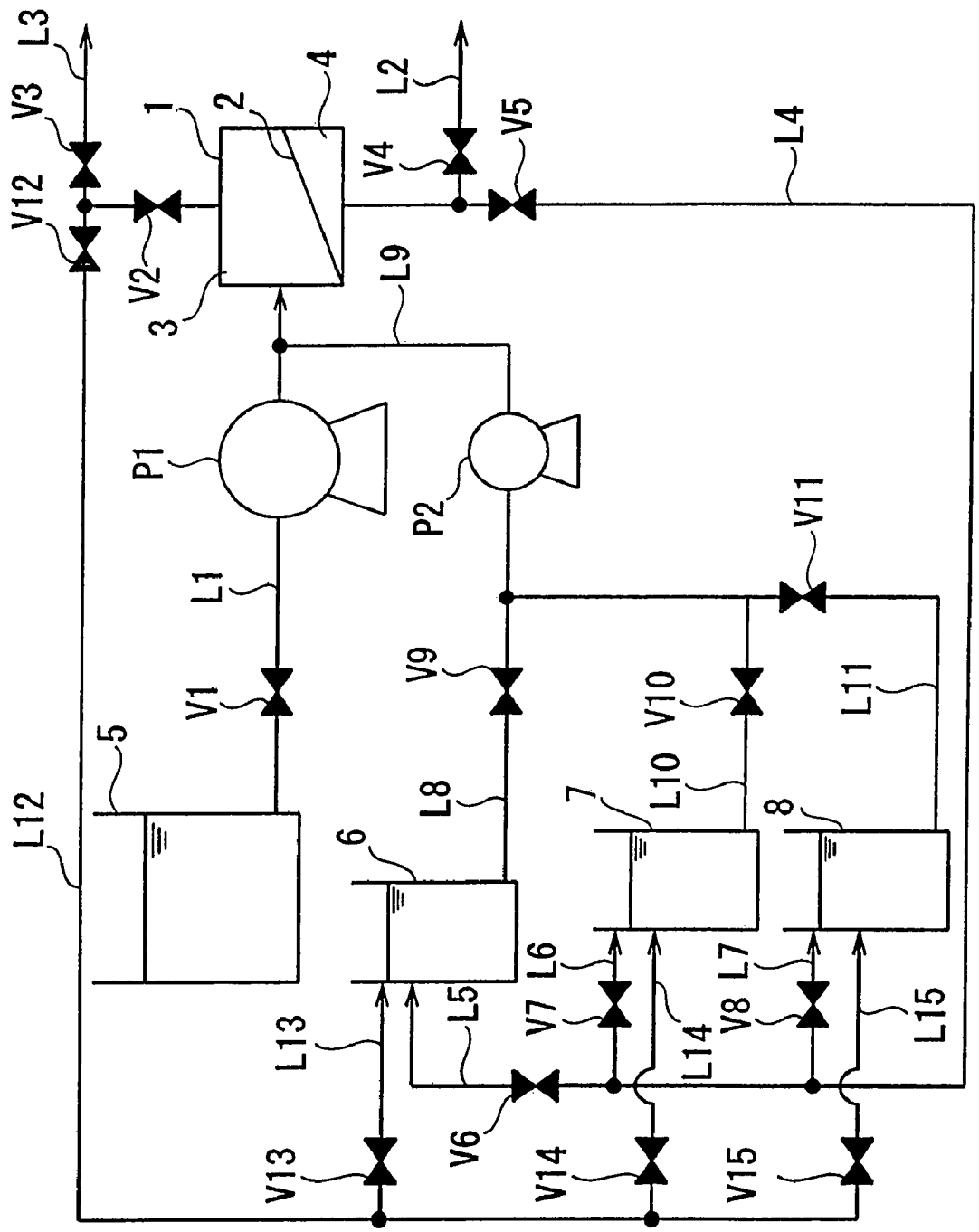
FIG. 1 is a flow diagram explaining the method for washing a selectively permeable membrane according to the present invention in a mode of embodiment.

FIG. 1 is a flow diagram explaining the method for washing a selectively permeable membrane according to the present invention in a mode of embodiment. In FIG. 1, 1 is a module in which a selectively permeable membrane 2 is arranged for partitioning a concentrate chamber 3 and a permeate chamber 4. 5 is a reservoir for the liquid-to-be-treated, 6 is a water tank, 7 is a washing liquid storage and 8 is an alkali storage. P1 is a high-pressure pump and P2 is a pump for a washing operation which may be operative under a pressure lower than that of P1. V1 to V15 each denote a valve and L1 to L15 each indicate a flow line.

In operating the selectively permeable membrane unit shown in FIG. 1 to effect membrane separation, the valves 1 to 4 are opened, while the other valves are held closed, whereupon the high-pressure pump 1 is actuated to cause the liquor-to-be-treated stored in the reservoir 5 to be supplied to the concentrate chamber 3 of the module 1 via the line L1 under a pressure, in order to cause selective permeation through the selectively permeable membrane 2, wherein the resulting permeate is guided from the permeate chamber 4 out via the line L2 as the treated liquor. The concentrate is discharged out from the concentrate chamber 3 via the line 3. On continuing this membrane separation, contaminant substances will adhere onto the selectively permeable membrane 2 and thereby the membrane performance, such as the flux and the selective permeability, decrease and, hence, the selectively permeable membrane should be subjected to washing.

When a reduction in the membrane performance, such as the flux, is detected upon the monitoring thereof, the washing liquid is supplied to the concentrate chamber 3 of the module 1 and washing of the selectively permeable membrane 2 is effected, in order to recover the membrane performance. For this, the valves V5 to V8 are opened while the valve V1 is kept closed so as to guide the treated liquor (treated water) through the lines L4 to L7 into the water tank 6, into the washing liquid storage 7 and into the alkali storage 8, respectively. Here, the washing liquid is prepared by introducing a polyol or a polyol plus an organic solvent into the washing liquid storage 7 and the alkali liquor is prepared by introducing an alkali into the alkali storage 8.

For carrying out washing with the washing liquid, valves V10, V2, V5, V7, V12 and V14 are opened while other valves are kept closed and the pump P2 for the washing operation is actuated so as to supply the washing liquid from the washing liquid storage 7 to the concentrate chamber 3 of the module 1 via the lines L10 and L9 to fill up the chamber 3 with the washing liquid for providing for washing of the selectively permeable membrane 2 by contacting it therewith. The washing may also be effected by circulating the washing liquid from the concentrate chamber 3 to the washing liquid storage 7 via the lines L12 and L14. When the washing is carried out by causing the washing liquid to permeate through the selectively permeable membrane 2 under pressure, the permeate is circulated from the permeate chamber 4 to the washing liquid storage 7 via the lines L4 and L6.

When an after-washing is carried out after the washing with the detergent, an alkali solution is supplied from the alkali storage 8 to the concentrate chamber 3 of the module 1 via the lines L11 and L9 by opening the valves V2, V8, V11, V12 and V15, so as to carry out the washing in the same way as in the case of washing with the detergent.

When a further washing with a washing liquid consisting of water (treated water) is to be effected after the washing with the detergent or with the washing liquid constituted of the alkali solution, the treated water is supplied as the washing liquid from the water tank 6 to the concentrate chamber 3 of the module 1 via the lines L8 and L9 by opening the valves V9, V2, V5, V6, V12 and V13 and actuating the pump P2 for washing operation, so as to carry out the washing in the same manner as in the case of washing with the detergent.

Since a detergent comprising a polyol having a molecular weight not higher than 400 is employed in the above-mentioned washing of the selectively permeable membrane 2, a high washing effect for the selectively permeable membrane is realized without causing any deterioration of the selectively permeable membrane together with safety to humans and to the environment with superior handling aspects, whereby a selectively permeable membrane exhibiting a deteriorated membrane performance, such as flux, can efficiently be washed within a brief time to recover the membrane performance. By effecting an after-washing with a washing liquid constituted of an alkali solution or water after the proper washing using the detergent, the remaining detergent and the detached remainder of the contaminants can be removed.

By using an organic solvent which exhibits a high detergent activity but may have an action of damaging the membrane or the membrane module at higher concentrations, such as an alcohol, ketone, ether or amide, in addition to the polyol, so as to maintain a concentration not causing deterioration of the membrane or the membrane module, a very high detergent activity is attained, whereby a higher detergent effect for the selectively permeable membrane will be realized.

While in the arrangement shown in FIG. 1, the treated liquor is used for the washing water, it is possible to employ an external supply of, for example, pure water, demineralized water or the like. For the water tank 6, washing liquid storage 7 and the alkali storage 8, one single vessel may be used in common without using each separate vessel.

EXAMPLES 1 AND 2 AND COMPARATIVE EXAMPLE 1

Figure 2:
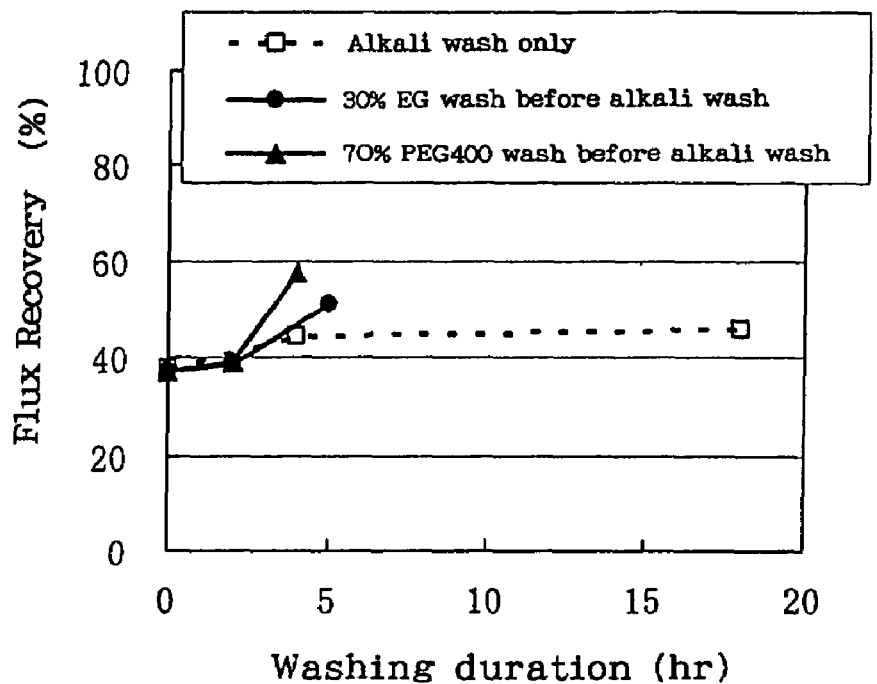
FIG. 2 shows the results of EXAMPLES 1 and 2 and of COMPARATIVE EXAMPLE 1 as to the degree of flux recovery in a graph.
Figure 3:
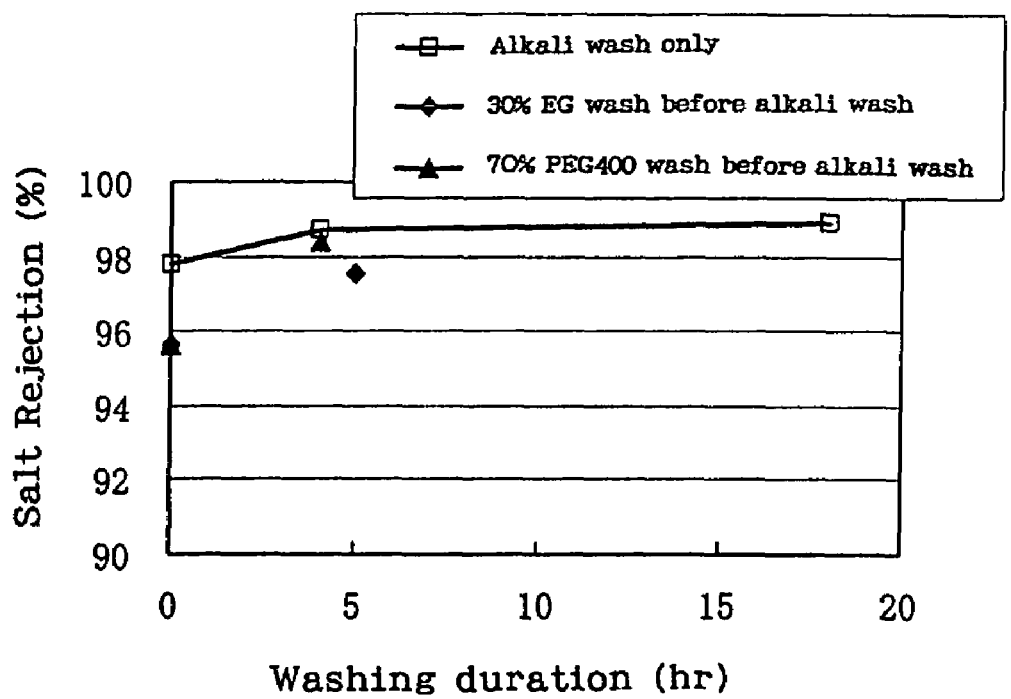
FIG. 3 shows the results of EXAMPLES 1 and 2 and of COMPARATIVE EXAMPLE 1 as to the degree of salt rejection in a graph.

Filtration was carried out using a reverse osmosis membrane NTR-759 HR of Nitto Electric Industrial Co., Ltd. under an operation pressure of 1.2 MPa for a treated water (with a COD not higher than 25 mg/liter) from a waste water treatment apparatus of a metal working factory as the liquor-to-be-treated. The flux was thereby decreased down to 30% of the original non-contaminated value. In EXAMPLE 1, a 30 wt. % aqueous solution of ethylene glycol was passed as the washing liquid to the membrane module for two hours, whereupon an alkaline aqueous solution of pH 12 was further passed thereto for three hours. In EXAMPLE 2, a 70 wt. % aqueous solution of a polyethylene glycol (PEG400) having an average molecular weight of 400 was passed as the washing liquid, whereupon an alkaline aqueous solution of pH 12 was further passed therethrough for two hours. In COMPARATIVE EXAMPLE 1, only an alkaline aqueous solution of pH 12 was passed as the washing liquid. The thereby obtained degree of flux recovery is shown in FIG. 2. From FIG. 2, it is seen that the flux recovery is attained within a more brief time and the degree of flux recovery is higher for the case where an alkaline washing was supplemented after the washing with ethylene glycol or polyethylene glycol (PEG400) than for the case where washing was effected only with an alkaline aqueous solution. In FIG. 3, the results of salt rejection (degree of desalting) for an aqueous sodium chloride solution of 500 mg/liter are shown, in which a salt rejection of 98% or higher is attained after the washing for each case, indicating that no debasement of the membrane performance occurred.

EXAMPLE 3 AND COMPARATIVE EXAMPLE 2

As the reverse osmosis membrane, a reverse osmosis membrane NTR-759 HR of Nitto Electric Industrial Co., Ltd. was employed. Filtration was carried out under an operation pressure of 1.2 MPa for a waste water (with a TOC of 20 mg/liter or less) from a machine parts production factory as the liquor-to-be-treated. For the membrane which had been used for service operation for a predetermined running time and the flux of which had been deteriorated, washing was carried out as COMPARATIVE EXAMPLE 2 using an aqueous sodium hydroxide solution prepared so as to adjust it to a pH of 12. By passing it through the membrane module for 7.5 hours, the flux was restored up to a value of 0.8 m$^3$/(m$^2$·day). Before and after the passing with the aqueous sodium hydroxide solution, pure water was passed therethrough for one hour. When the waste water was then filtered again for the predetermined running time, the flux decreased and, therefore, as in EXAMPLE 3, a liquid mixture of 70 wt. % of ethylene glycol and 30 wt. % of methanol was passed therethrough as the washing liquid for two hours, followed by passing with pure water for one hour. The original flux for pure water of this membrane before the service use was 1 m³/(m²·day) and the membrane was not recovered completely by only the alkaline washing and water-washing for a washing duration of 9.5 hours, whereas the flux was recovered completely by washing with the liquid mixture of ethylene glycol and methanol for only a washing duration of 3 hours. By the way, salt rejection was observed using an aqueous sodium chloride solution of 500 mg/liter, whereby a value of 98.0% before the experiment and a value of 97.5% after the experiment were obtained, showing almost no change.

EXAMPLE 4

Figure 4:
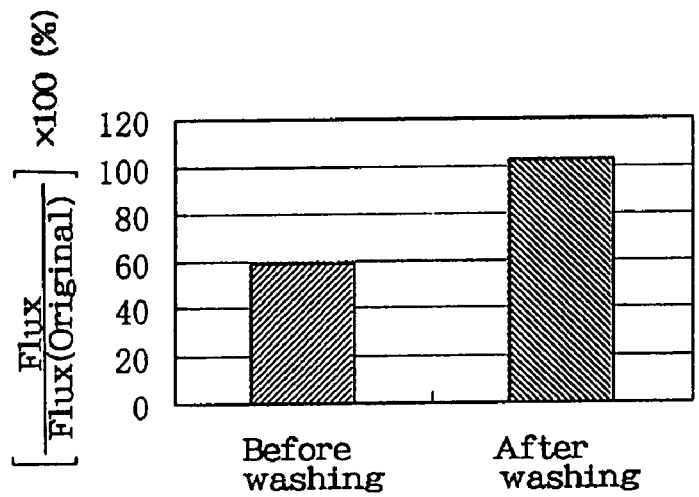
FIG. 4 shows the result of EXAMPLE 4 as to the degree of flux recovery in a graph.

A treatment was carried out under the same condition as in EXAMPLE 3 for a waste water (with a TOC of 20 mg/liter or less) from a machine parts production factory as the liquor-to-be-treated, whereby the flux was decreased and, therefore, a liquid mixture of 70 wt. % of glycerin and 30 wt. % of methanol was passed therethrough for an hour, followed by passing with pure water for an hour. The degree of flux recovery before and after the washing is shown in FIG. 4. From FIG. 4, a high degree of flux recovery can be recognized.

EXAMPLES 5 TO 8 AND COMPARATIVE EXAMPLE 3

Figure 5:
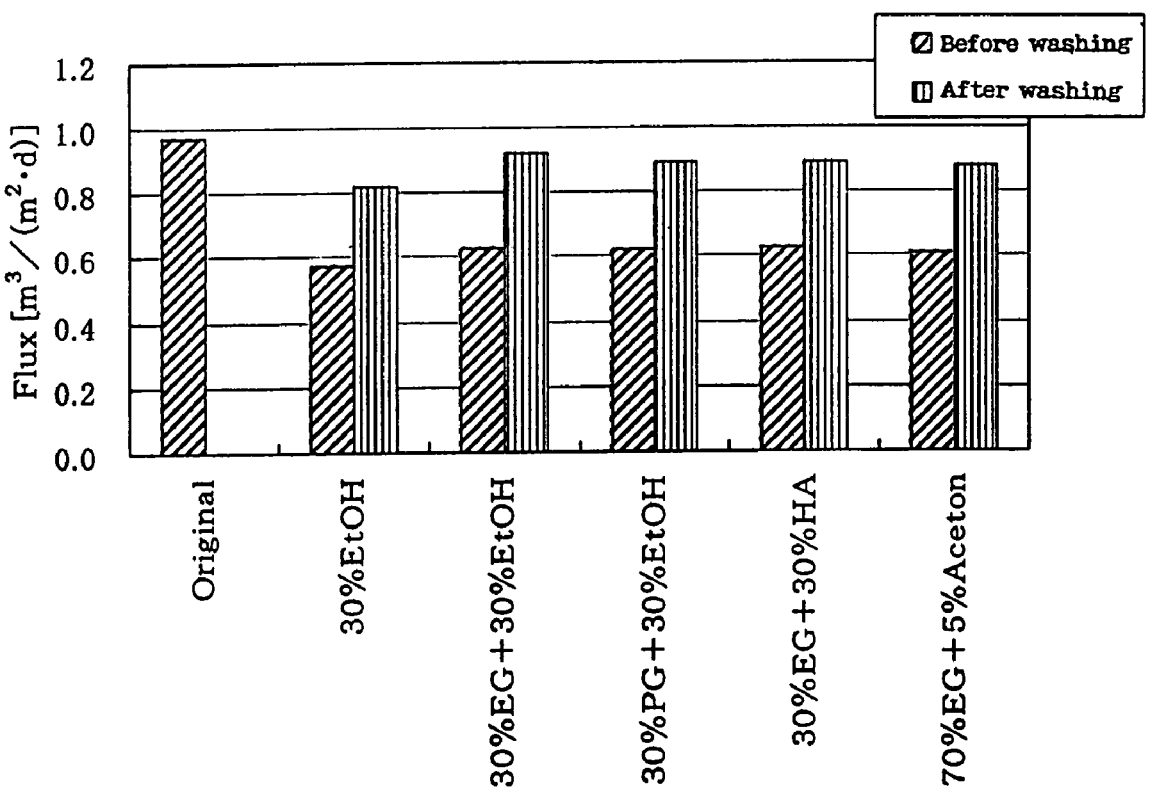
FIG. 5 shows the results of EXAMPLES 5 to 8 and of COMPARATIVE EXAMPLE 3 as to the flux in a graph.

In the procedures of EXAMPLE 4, there was each used as the washing liquid, a liquid mixture of 30 wt. % of ethylene glycol (EG) and 30 wt. % of ethanol (EtOH) (for EXAMPLE 5); a liquid mixture of 30 wt. % of propylene glycol (PG) and 30 wt. % of ethanol (EtOH) (for EXAMPLE 6); a liquid mixture of 30 wt. % of ethylene glycol (EG) and 30 wt. % of formamide (HA) (for EXAMPLE 7); a liquid mixture of 70 wt. % of ethylene glycol (EG) and 5 wt. % of acetone (Aceton) (for EXAMPLE 8); and a liquid of 30 wt. % of ethanol (EtOH) (for COMPARATIVE EXAMPLE 3), each of which was passed for one hour, followed by passing of pure water for one hour. The flux before and after the washing is shown in FIG. 5. From FIG. 5, it is seen that a more higher degree of flux recovery is recognized for EXAMPLES 5 to 8 than for COMPARATIVE EXAMPLE 3. In FIG. 5, "Original" indicates the original value of flux before use (REFERENCE EXAMPLE).

COMPARATIVE EXAMPLE 4

A membrane of NTR-759 HR of Nitto Electric Industrial Co., Ltd., which had been used for filtration of a waste water containing a nonionic surfactant as the liquor-to-be-treated and had suffered from deterioration of the flux thereof by being decreased to a value of 0.6 m³/(m²·day), was washed with a 60 wt. % methanol solution, whereby the flux was recovered to about 0.9 m³/(m²·day) and the degree of salt rejection was decreased from 98% to a value of 93%.

COMPARATIVE EXAMPLE 5

The durability of the module was examined using an aqueous acetone solution as the liquor-to-be-treated. As the membrane module, a 4 inch NTR-759 HR module (of Nitto Electric Industrial Co., Ltd.) was used. While there was no problem at an acetone concentration of 5% by weight of the aqueous acetone solution and passing was permitted even at a concentration of 10% by weight, the module was destroyed and the liquor-to-be-treated flowed out untreated to the permeate side when the concentration was increased to 30% by weight.

EXAMPLES 9 AND 10

Figure 6:
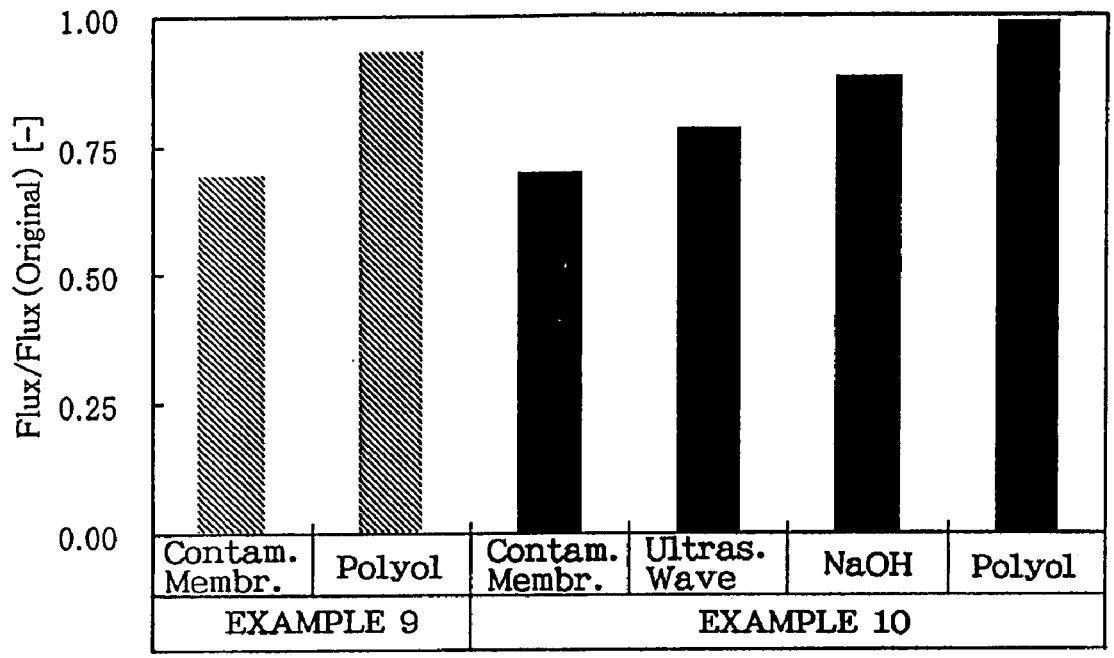
FIG. 6 shows the results of EXAMPLES 9 and 10 as to the degree of flux recovery in a graph.

Filtration was carried out using a reverse osmosis membrane SU-720 P of Toray Industries, Inc. under an operation pressure of 1.5 MPa for a treated water (with a COD of 30 mg/liter or less) from a waste water treatment apparatus of a printing ink production factory as the liquor-to-be-treated. The flux was decreased thereby down to 50% of the value before being contaminated. In EXAMPLE 9, a mixed liquid of 70 wt. % of ethylene glycol and 30 wt. % of methanol was used as the washing liquid. After soaking therein for one hour, passing of pure water was carried out for one hour. In EXAMPLE 10, an alkaline solution of pH 12 was passed for a period of 15 hours after having been subjected to irradiation of ultrasonic wave for 5 minutes under soaking in pure water, followed by soaking in a mixed liquid of 70 wt. % of ethylene glycol and 30 wt. % of methanol as the washing liquid, whereupon pure water passing was carried out for one hour. The degree of flux recovery for an aqueous solution of sodium chloride of 500 mg/liter after each washing operation is shown in FIG. 6. While a recovery of the flux is attained by the washing operation in EXAMPLE 9, a more higher value of flux is attained by the washing operation of EXAMPLE 10 due to a synergistic effect with other washing method.

EXAMPLES 11 AND 12

A reverse osmosis membrane of NTR-759 HR of Nitto Electric Industrial Co., Ltd. was used for carrying out filtration of a waste water containing a nonionic surfactant as the liquor-to-be-treated under an operation pressure of 1.2 MPa. The flux was thereby decreased down to 0.2 m³/(m²·day). In EXAMPLE 11, the membrane module was immersed in a liquid mixture of 70 wt. % of ethylene glycol and 30 wt. % of methanol as the washing liquid for 1.5 hours, whereupon pure water passing was carried out for one hour. In Example 12, the membrane module was immersed in a liquid mixture of 50 wt. % of ethylene glycol, 20 wt. % of diethylene glycol and 30 wt. % of methanol as the washing liquid for 1.5 hours, whereupon pure water passing was carried out for one hour. The flux for pure water after the washing was restored up to 83% and 100% in Examples 11 and 12, respectively. While the flux was restored by using the composition of EXAMPLE 11, a more higher detergent effect was attained in EXAMPLE 12. This is assumed to be due to that the solubility of the nonionic surfactant in the washing liquid is increased by replacing a part of ethylene glycol with diethylene glycol.

EXAMPLE 13

A reverse osmosis membrane of NTR-759 HR of Nitto Electric Industrial Co., Ltd. was used for carrying out filtration of a city sewage as the liquor-to-be-treated under an operation pressure of 1.5 MPa. A membrane module of which flux had been decreased by a decrement of 18% was immersed in a mixed liquid of 10 wt. % erythritol and 30 wt. % ethanol as the washing liquid for one hour, whereupon pure water passing was carried out for 5 hours. The flux was recovered by an increment of about 15% and reached nearly the original value.

EXAMPLES 14 AND 15

Filtration was carried out using a reverse osmosis membrane SU-720 P of Toray Industries, Inc. under an operation pressure of 1.5 MPa for a treated water (with a COD of 30 mg/liter or less) from a waste water treatment apparatus of a printing ink production factory as the liquor-to-be-treated.

Figure 7:
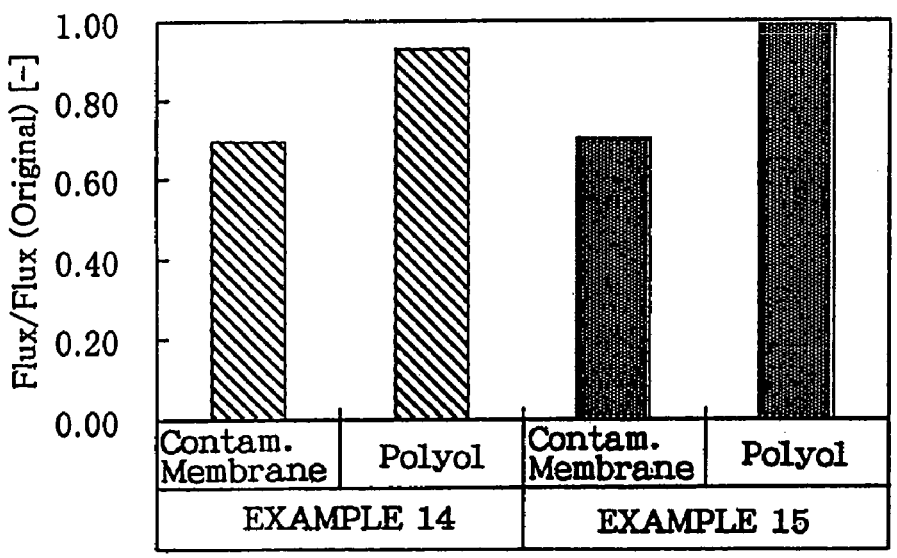
FIG. 7 shows the results of EXAMPLES 14 and 15 as to the degree of flux recovery in a graph.

The flux was decreased thereby down to 50% of the value before being contaminated. In EXAMPLE 14, a mixed liquid of 70 wt. % of ethylene glycol and 30 wt. % of methanol was used as the washing liquid. After soaking therein for one hour, passing of pure water was carried out for one hour. In EXAMPLE 15, a mixed liquid of 68 wt. % of ethylene glycol, 30 wt. % of methanol and 2 wt. % of acetylacetone was used as the washing liquid. After soaking therein for one hour, pure water passing was carried out for one hour. The degree of flux recovery for an aqueous solution of sodium chloride of 500 mg/liter after each washing operation is shown in FIG. 7. While a flux recovery was attained by the washing operation in EXAMPLE 14, a more higher value of flux was attained by the washing operation of EXAMPLE 15. This is assumed to be due to an increase in the solubility of membrane-contaminants in the washing liquid by the addition of acetylacetone.

EXAMPLE 16

Figure 8:
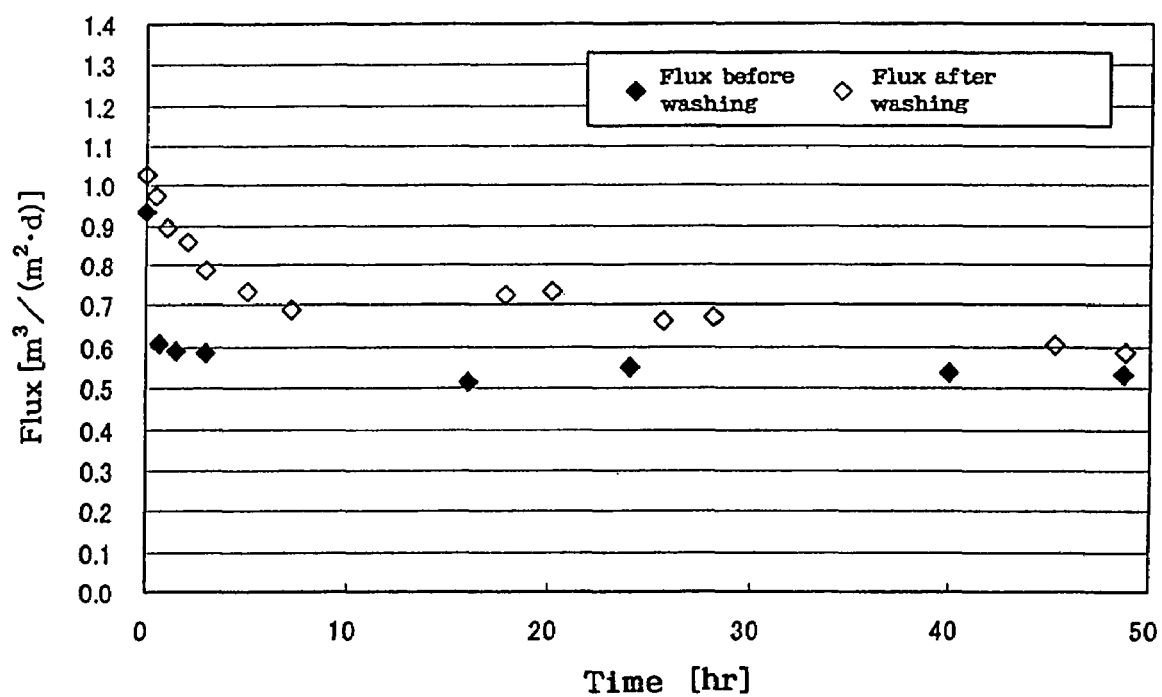
FIG. 8 shows the result of EXAMPLE 16 as to the flux in a graph.

A reverse osmosis membrane of NTR-759 HR of Nitto Electric Industrial Co., Ltd. was used for carrying out filtration of a waste water from a machine parts production factory as the liquor-to-be-treated (with a TOC of 12 mg/liter) under an operation pressure of 1.2 MPa for 50 hours. The flux was decreased down to a value of 0.55 $m^3/(m^2 \cdot day)$ as shown in FIG. 8. Then, soaking in a liquid mixture of 70 wt. % of ethylene glycol and 30 wt. % of methanol was effected for one hour, whereupon pure water passing was carried out for one hour. After the washing, filtration of the same liquor-to-be-treated was performed again. A more higher value of primary flux than that before the washing was obtained and higher flux values were able to be attained over a period of 50 hours. The degree of salt rejection was detected to be 99% for both the cases.

APPLICABILITY IN INDUSTRY

The present invention is utilized as a detergent for the washing of selectively permeable membranes, such as a reverse osmosis membrane, nano-filtration membrane and so on, as well as for a method of washing with the detergent.

The invention claimed is:

1. A method for washing a selectively permeable membrane composed of a reverse osmosis membrane exhibiting deteriorated permeation flow flux due to adhesion thereto of a contaminant substance, comprising washing the membrane with a washing liquid consisting of a polyol having a molecular weight not greater than 400 and, optionally, an organic solvent.

2. The method as claimed in claim 1, wherein the washing liquid contains an organic solvent.

3. The method as claimed in claim 1, wherein the membrane is subjected, before and/or after the washing with the washing liquid, to a pretreatment washing and/or an after-treatment washing by another washing method.

4. The method as claimed in claim 1, wherein the washing is performed by contacting the washing liquid with the selectively permeable membrane.

5. The method as claimed in claim 1, wherein the polyol is selected from the group consisting of ethylene glycol, diethylene glycol, propylene glycol, glycerin, polyglycols and sugar alcohols.

6. The method as claimed in claim 2, wherein the organic solvent comprises a compound selected from the group consisting of monohydric alcohols, ethers, ketones and amides.

* * * * *